(12) United States Patent
Tartour

(10) Patent No.: US 8,685,408 B2
(45) Date of Patent: Apr. 1, 2014

(54) COMPOSITIONS COMPRISING A B SUBUNIT OF SHIGA TOXIN AND A MEANS STIMULATING NKT CELLS

(75) Inventor: Eric Tartour, Paris (FR)

(73) Assignees: Universite Rene Descartes Paris 5, Paris (FR); Institut Curie, Paris (FR); Assistance Publique Hopitaux de Paris, Paris (FR); Centre National de la Recherche Scientifique-CNRS, Paris (FR)

( * ) Notice: Subject to any disclaimer, the term of this patent is extended or adjusted under 35 U.S.C. 154(b) by 476 days.

(21) Appl. No.: 12/521,404

(22) PCT Filed: Dec. 26, 2007

(86) PCT No.: PCT/EP2007/064556
§ 371 (c)(1),
(2), (4) Date: Mar. 11, 2010

(87) PCT Pub. No.: WO2008/080926
PCT Pub. Date: Jul. 10, 2008

(65) Prior Publication Data
US 2010/0196417 A1    Aug. 5, 2010

Related U.S. Application Data

(60) Provisional application No. 60/877,354, filed on Dec. 28, 2006.

(30) Foreign Application Priority Data

Dec. 28, 2006    (EP) ..................................... 06292066

(51) Int. Cl.
*A61K 39/385*    (2006.01)

(52) U.S. Cl.
USPC .................................................... 424/197.11

(58) Field of Classification Search
None
See application file for complete search history.

(56) References Cited

U.S. PATENT DOCUMENTS

| | | | |
|---|---|---|---|
| 7,632,514 B2 * | 12/2009 | Johannes et al. | ........... 424/236.1 |
| 2008/0069832 A1 | 3/2008 | Chomez et al. | |
| 2010/0028415 A1 * | 2/2010 | Haynes et al. | ................ 424/450 |

FOREIGN PATENT DOCUMENTS

| | | |
|---|---|---|
| WO | 99/52547 A1 | 10/1999 |
| WO | 03/009812 A | 2/2003 |
| WO | 2005/112991 A | 12/2005 |

OTHER PUBLICATIONS

Haicheur et al, J. Immunology, 2000, 165:3301-3308.*
Kawano et al. (International Immunology, vol. 11, No. 6, pp. 881-887, 1999).*
Fujii et al. ( J. Exp. Med., vol. 198, No. 2 Jul. 2003).*
Croudace J. et al., "An Assessment of iNKT and TLR4 ligand combinations as adjuvants to promote antigen-presentation by human dendritic cells for use in anti-cancer DC immunotherapy", Immunology, vol. 116, No. Suppl. 1, Dec. 2005, pp. 100-101, XP002474824, abstract.
Ogawa et al., "Immunological activities of chemically defined lipid A from Helicobacter pylori LPS in comparison with *Porphyromonas gingivalis* lipid A and *Escherichia coli*-type synthetic lipid A (compound 506)", Vaccine, Butterworth Scientific. Guildford, GB, vol. 15, No. 15, Oct. 1997, pp. 1598-1605, XP004091928.

* cited by examiner

*Primary Examiner* — Gary Nickol
*Assistant Examiner* — Khatol Shahnan-Shah
(74) *Attorney, Agent, or Firm* — Gottlieb, Rackman & Reisman, P.C.

(57) ABSTRACT

The present invention relates to a composition comprising a) a B subunit of Shiga toxin or a functional equivalent thereof which is able to bind the Gb3 receptor, complexed with an antigen and b) at least one ligand of CDI capable of stimulating NK T cells; and to a pharmaceutical composition and a medicament comprising said composition.

24 Claims, 9 Drawing Sheets

Figure 1:
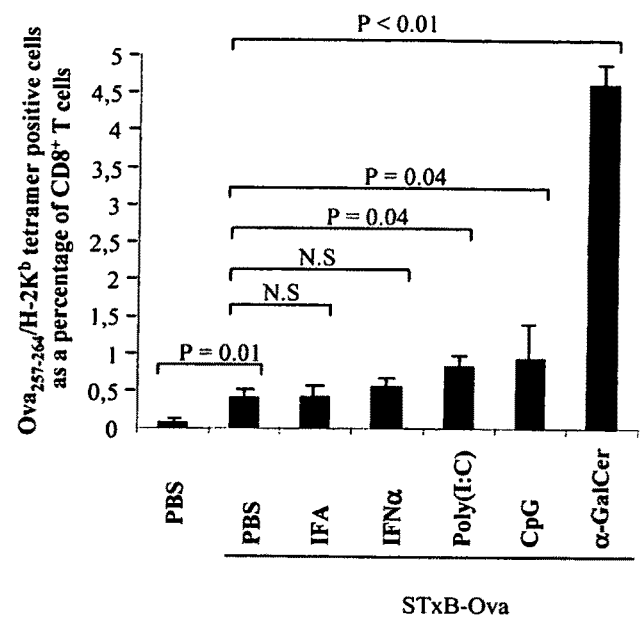

COMPOSITIONS COMPRISING A B SUBUNIT OF SHIGA TOXIN AND A MEANS STIMULATING NKT CELLS

CROSS-REFERENCE TO RELATED APPLICATIONS

This application claims the benefit of prior U.S. Provisional Patent Application Ser. No. 60/877,354, filed Dec. 28, 2006.

SEQUENCE LISTING

The instant application contains a Sequence Listing which has been submitted in ASCII format via EFS-Web and is hereby incorporated by reference in its entirety. Said ASCII copy, created on Jun. 18, 2012, is named B09754BB_JAZ_ST25.txt and is approximately 2 kilobytes in size.

FIELD OF THE INVENTION

The present invention relates to the field of antigen-related disease and especially to the field of therapeutic vaccines. In particular, the present invention aims to elicit an immune response in an individual in need thereof, using a B subunit of Shiga toxin or a functional equivalent thereof complexed to an antigen and a means stimulating NKT cells.

BACKGROUND OF THE INVENTION

Vaccine delivery system and adjuvants approved for human use (aluminium salts, MF59, virosomes . . . ) primarily stimulate humoral immune responses. However, preclinical studies strongly suggest that successful vaccines against pathogens (HIV, *mycobacterium tuberculosis*, malaria . . . ) but also cancer vaccines will likely require both humoral and cellular responses. Live attenuated pathogens or whole inactivated organisms have been shown to activate both arms of the immune system in human but these vaccines are difficult to produce, potentially unsafe or poorly immunogenic. Development of subunit vaccines to elicit a robust specific CD8+ T cell response represents therefore an ongoing competitive challenge.

Dendritic cells (DCs) have been shown to be the most potent antigen-presenting cells for the induction of primary T cell responses, but they can also induce the differentiation of B cells into antibody forming cells and mobilize other effective immune cells such as NK and NKT cells. In human, clinical studies using healthy recipients proved the immunogenicity and safety of DCs, and demonstrated that a single injection of a small number of antigen-pulsed DCs is sufficient to rapidly expand T-cell immunity for both naïve and recall antigens. However, generation and ex vivo manipulation of DCs are laborious. Direct antigen targeting to DCs in vivo will therefore offer several advantages.

Therefore, a composition that elicits a robust specific CD8+ T cell response in vivo is of great concern in the field of therapeutic vaccines. The present invention aims to respond to said objective by providing a composition that delivers antigen to DCs, leads to an optimal presentation of peptides derived from the antigen by HLA-class I molecules, and provides a maturation stimulus for DCs.

WO02/060937 previously disclosed a carrier for targeting a molecule to Gb3 receptor expressing cells, said carrier having the following formula STxB-Z(n)-Cys, wherein STxB is the Shiga Toxin subunit B, Z is an amino acid linker with no sulfydryl group, n being 0, 1 or a polypeptide, and Cys is the amino acid Cysteine. WO02/060937 showed that a STxB based vaccine induced humoral response and a robust and long-lasting CD8+ T cell response. All these results may be explained by the ability of STxB to increase costimulatory and MHC class II molecules on DCs and to induce TNF on some cells which could indirectly favour the maturation of DCs. However, when myeloid DCs derived from bone marrow were incubated with STxB, no maturation of these cells has been observed. Thus, the STxB based vaccine disclosed in WO02/060937 does not lead to the maturation of DCs in vivo.

In one aspect, the present invention aims therefore to provide a composition that leads to the maturation of DCs.

Combinations of vectors complexed to an antigen with adjuvants have already been described, as adjuvants are known to favour DCs maturation.

For example, EP 1078007 described the use of a toxin-antigen conjugate, wherein the toxin is the Shiga toxin B subunit, in combination with KLH for stimulating an immune response.

In addition, the patent application WO2005/112991 disclosed the use of the B subunit of Shiga Toxin complexed with an antigen and an adjuvant for stimulating an immune response. The adjuvant may be selected from the group consisting of metal salts, oil in water emulsions, Toll like receptors agonists, saponins, lipid A, alkyl glucosaminide phosphate, immunostimulatory oligonucleotide or combinations thereof.

However, the Applicant observed and confirmed that all combinations of vectors and adjuvant are not equivalent for the induction of CD8+ T cells response. After screening many conventional adjuvants, the inventors found a dramatic synergy between ligands of CD1 capable of stimulating NKT cells and the STxB based vaccine, leading to potent CD8+ T cells response with the use of very low doses of antigen. Vaccines combining STxB and one of said ligands were found to be efficient to break tolerance against self antigen and to elicit anti-viral immunity. Contrary to the teaching of the prior art, this synergy was not observed with all adjuvants. In particular, the Applicant did not observed such a synergy with adjuvants such as IFA (Haicheur et al. JI 2000, 165: 3301-3308) and observed a very weak synergy with adjuvants such as IFNα, Poly(I:C), or the Toll like receptor agonist CpG.

SUMMARY OF THE INVENTION

Therefore, an object of the present invention is to provide a composition comprising
a) a B subunit of Shiga toxin or a functional equivalent thereof which is able to bind the Gb3 receptor, complexed with an antigen and
b) at least one ligand of CD1 capable of stimulating NK T cells.

In one embodiment of the invention, the immunological functional equivalent of the B subunit of Shiga toxin has at least 50% amino acid sequence identity to the B subunit of Shiga toxin.

In another embodiment of the invention, said ligand of CD1 is a ligand of CD1d.

In another embodiment of the invention, said ligand of CD1 is a glycolipid or phospholipid, a glycosphingolipid, a derivative or an analog thereof. In a preferred embodiment, said ligand is chosen from iGb3, GD3, PE and PI.

In another preferred embodiment, said ligand of CD1 is a glycosylceramide or an analog or a derivative thereof. Preferably, said glycosylceramide is selected from the group consisting of α-GalCer, α-GlcCer, Galα1-6Galα1-1'Cer, Galα1-6Glcα1-1'Cer, Galα1-2Galα1-1'Cer, Galβ1-3Galα1-1'Cer or a derivative thereof, preferably a C-glycoside derivative thereof, more preferably a C-glycoside derivative of α-GalCer.

In one embodiment of the invention, αGalCer is (2S,3S,4R)-1-O-(α-D-galactopyranosyl)-2-(N-hexa-cosanoylamino)-1,3,4-octadecanetriol. In another embodiment, αGalCer is (2S,3S,4S)-1-O-(α-D-galactopyranosyloxy)-2-hexacosanoylamino-3,4-octadecanediol (KRN7000).

In a preferred embodiment of the invention, said ligand of CD1 is selected from the group consisting of 3-O-sulfo-α-GalCer, β-GalCer, an OCH compound, α-C-GalCer.

In another embodiment, said ligand of CD1 is a microbe derived glycolipid. Preferably, said ligand is
- a *Sphingomonas* species-derived glycosphingolipid selected in the group consisting of GSL-1 and GSL'1 or
- a *Borrelia* species derived glycolipid selected from the group consisting of BbGL-I and BbGL-II or
- a *Mycobacteria* species derived phosphoglycolipid PIM.

Figure 3:
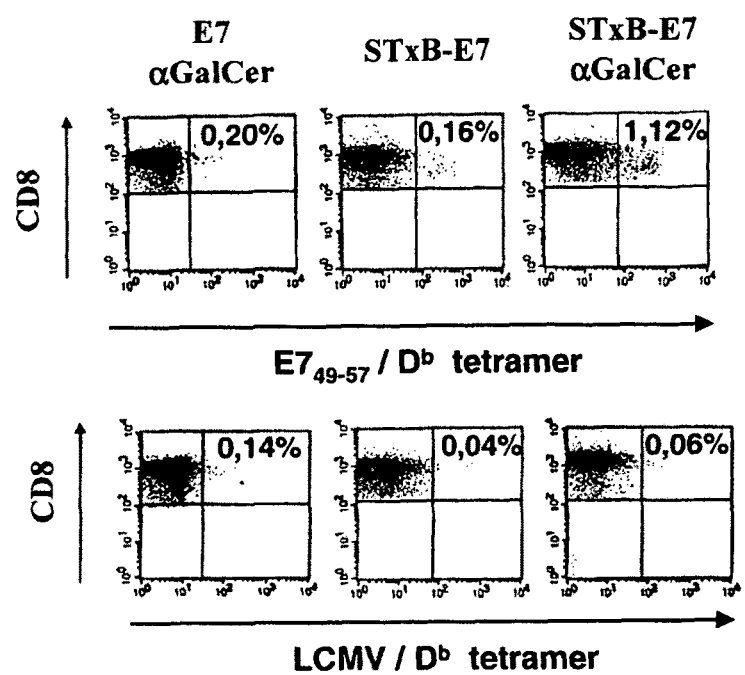

In one embodiment of the invention, the B subunit of Shiga toxin or the functional equivalent thereof is present in a universal polypeptidic carrier having the formula STxB-Z(n)-Cys, wherein

- STxB is the Shiga Toxin B subunit or a functional equivalent thereof,
- Z is an amino-acid devoided of sulfydryl group, n being 0, 1 or a polypeptide,
- Cys is the amino-acid Cysteine.

In a preferred embodiment, n is 0.

In a preferred embodiment, the antigen is covalently linked to the —S residue of the universal carrier by a —S—S, or —S—CO, or S—$CH_2$, or —S—NH linkage. In another preferred embodiment, the universal carrier is covalently linked to an oligopeptide or a polypeptide by a —S—S, or —S—CO, or S—$CH_2$, or —S—NH linkage, and the antigen to be targeted is operably linked to the said oligopeptide or polypeptide. In a more preferred embodiment, the universal carrier is covalently linked to a poly-lysine oligopeptide and the antigen to be targeted is operably linked to the said poly-lysine moiety.

In one embodiment of the invention, the antigen is a tumor antigen, a viral or a bacterial antigen.

In one embodiment of the invention, the composition as described above further comprises a pharmaceutically acceptable carrier.

The present invention also aims to provide a medicament comprising a composition as described above.

Another object of the present invention is a vaccine comprising said composition.

It is also an object of the present invention to provide a pharmaceutical kit comprising:

a) a first container comprising a B subunit of Shiga toxin or a functional equivalent thereof which is able to bind the Gb3 receptor, complexed with an antigen and b) at least a second container comprising at least one ligand of CD1 capable of stimulating NK T cells.

The present invention relates to the use of a composition as described above for the manufacture of a pharmaceutical composition or a medicament, including a vaccine, for treating an antigen-related condition in an individual, said antigen-related state being a tumor or an infection.

In one embodiment, the present invention relates to the use of said composition for treating an antigen-related condition in an individual in need thereof, wherein said composition is to be administrated to said individual in an therapeutically effective amount for stimulating an immune response against the antigen in said individual, thereby treating said antigen-related condition in said individual.

In another embodiment, the present invention relates to the use of said composition for treating an antigen-related condition in an individual in need thereof, wherein said composition is to be administered in combination with thalidomide or an analog thereof, preferably lenalidomide.

The present invention also relates to the use of the kit as described above, wherein at least one ligand of CD1 capable of stimulating NK T cells is to be administrated before, simultaneously or after the B subunit of Shiga toxin or a functional equivalent thereof which is able to bind the Gb3 receptor, complexed with an antigen.

In one embodiment, the use of the composition as described above leads to the stimulation of the immune response, which comprises stimulating dendritic cells.

In another embodiment, the use of the composition as described above leads to the stimulation of the immune response, which comprises eliciting an antigen specific CD8 response.

BRIEF DESCRIPTION OF THE DRAWINGS

FIG. 1: Role of adjuvants on the levels of anti-$OVA_{257-264}$ $CD8^+$T cells induced by the STxB-OVA conjugate. Mice were subcutaneously immunized twice (d0 and d21) with STxB-OVA alone (50 μg=0.5 nmol) diluted in PBS or combined with various adjuvants (IFA vol/vol, IFNα 100000 IU d0, d1 and d2, Poly(I:C)(250 μg, d0 and d21), CpG (50 μg, d0 and d21). α-GalCer (2 μg) was only admixed with STxB-OVA on d0. The second immunization was performed with STxB-OVA alone. $CD8^+$T cells from spleen were isolated 7 days after the last immunization and directly stained ex vivo with PE-labeled $OVA_{257-264}/k^b$ tetramer and allophycocyanin-labeled anti-CD8 mAb. Values shown correspond to mean±SD obtained with specific tetramer after subtracting values from irrelevant tetramer recognizing a VSV-derived peptide in the context of $K^b$. These results are representative of three experiments with 4 mice per group.

FIG. 2: α-GalCer increases the efficiency of STxB to induce long-lasting and functional specific anti-$OVA_{257-264}$ $CD8^+$T cells even at very low doses of antigen. Mice were subcutaneously immunized twice (d0 and d21) with various doses of STxB-OVA alone (A Left) or combined with α-GalCer (A right, C, D) or with free ovalbumin admixed with α-GalCer (B). As mentioned in Material and Methods, α-GalCer was only administered during the first immunization. A, B, C: $CD8^+$T cells from spleens were isolated 7 days after the last immunization and directly stained ex vivo with PE-labeled $OVA_{257-264}/k^b$ tetramer and allophycocyanin-labeled anti-CD8 mAb. Results shown are gated on $CD8^+$T cells. An irrelevant tetramer recognizing a VSV-derived peptide in the context of $K^b$ and an isotype control mAb were included as controls. These results are representative of three experiments with 4 mice per group. D: Mice were immunized with STxB-OVA (1 μg) mixed with α-GalCer (2 μg). Left: IFNγ producing $OVA_{257-264}/K^b$ specific $CD8^+$ T cells were detected ex vivo by an IFNγ ELISPOT assay using EL4 pulsed (■) or not (□) with the $OVA_{257-264}$ peptide (SL8). SFC=spot-forming cells were read using an Elispot automated reader system. Right: CTL activity was measured in a standard 4-h $^{51}Cr$ release assay on the target EL4 cells pulsed with (■) or without (□) the $OVA_{257-264}$ peptide at an effector-target E/T ratio of 100/1. Three mice per group were immunized and these experiments were reproduced two times.

FIG. 3: α-GalCer also increases the efficiency of STxB-E7 to elicit anti-E7 CTL. Mice were immunized on day 0 and day 21 with STxB-E7$_{43-57}$ (1 μg) alone or mixed with α-GalCer or with the free polypeptide E7$_{43-57}$ mixed with α-GalCer. Seven days after the last immunization, CD8$^+$ T cells from spleen were isolated and directly stained with PE-labeled E7$_{49-57}$/D$^b$ tetramer. (Cells were previously gated on CD8$^+$ T cells). An irrelevant tetramer recognizing a LCMV derived peptide in the context of Db was included as controls. These results are representative of two experiments with 3 mice per group.

Figure 4:
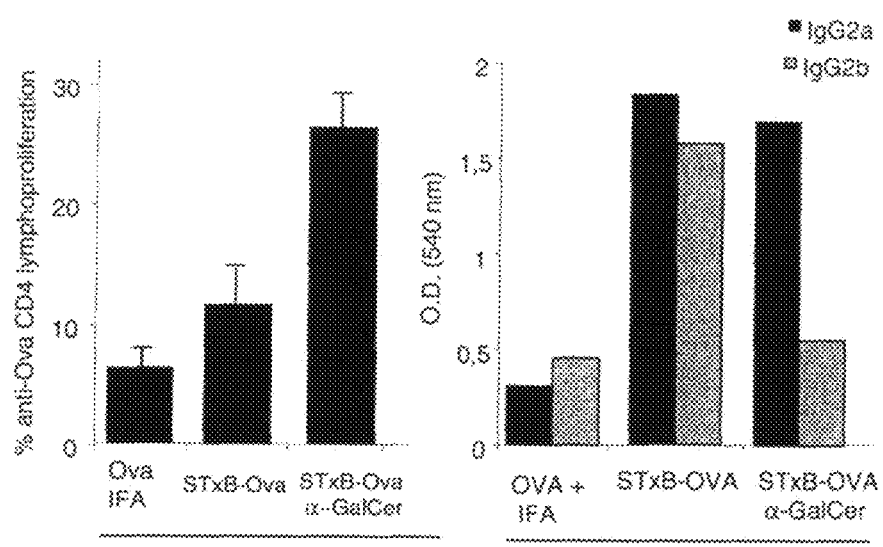

FIG. 4: CD4$^+$T cell and humoral responses after STxB-OVA based vaccine immunization. Left: Mice (n=3 per group) were immunized twice (d0 and d21) with STxB-OVA (0.01 nmol) alone or combined with α-GalCer (2 μg). As control, mice were vaccinated with ovalbumin (0.01 nmol) mixed with IFA. Seven days after the last immunization, CD4$^+$T cells were purified from spleen and labeled with CFSE. They were then incubated with T cell depleted splenocytes as APC pulsed with free ovalbumin protein and cocultured for 5 days in AIM V serum free medium. Proliferation in the absence of APC sensitization was subtracted as background from values obtained after ovalbumin pulsing. These experiments were reproduced two times. Right: One week after the last immunization, serum was collected and anti-OVA IgG2a and IgG2b were measured by ELISA.

Figure 5:
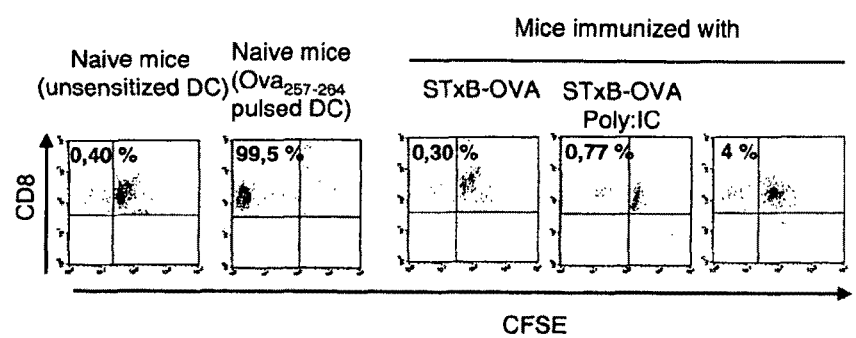

FIG. 5: Combination of STxB-OVA and α-GalCer enhances the cross-presentation of ovalbumin by dendritic cells. Mice (n=3 per group) were immunized with STxB-OVA alone (1 μg=0.01 nmol) or combined with Poly (I:C) or with α-GalCer (2 μg). Seven days after vaccination, CD11c$^+$ enriched dendritic cells were cocultured with CFSE labeled OT-1 cells for 72 hours. These experiments were reproduced three times with similar results. Dot plots were gated on CFSE labeled CD8$^+$ T-1 cells.

Figure 6:
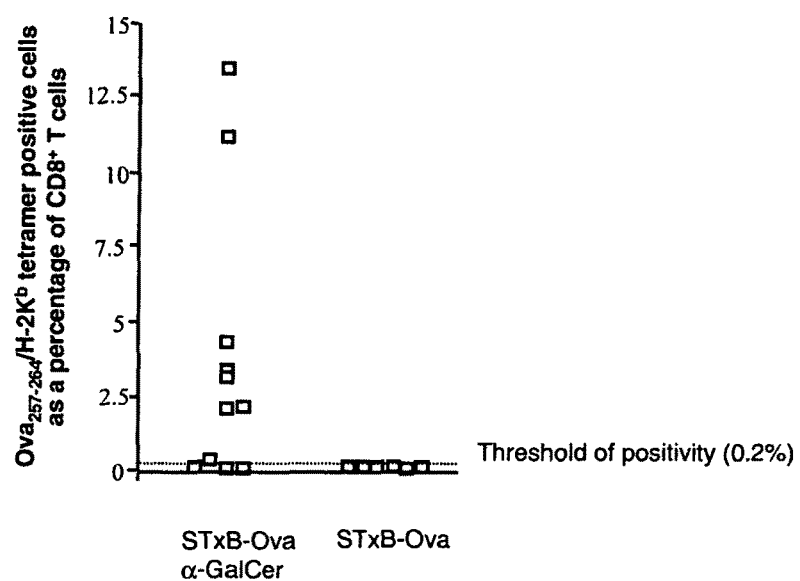

FIG. 6: STxB-OVA combined with α-GalCer primes anti-OVA$_{257-264}$ CD8$^+$T cells in OVA-TG mice.

OVA-TG mice were immunized with STxB-OVA (0.1 nmol) combined or not with α-GalCer (2 μg). Fourteen days later, CD8$^+$ T cells from spleen were isolated and directly stained with PE-labeled OVA$_{257-264}$/K$^b$ tetramer and APC-labeled anti-CD8 mAb. Each square represents values from individual mice and corresponds to results obtained with specific OVA$_{257-264}$/K$^b$ tetramer after subtracting the values obtained with an irrelevant tetramer recognizing a VSV derived peptide in the context of K$^b$. Two series of experiments were performed with similar results.

Figure 7:
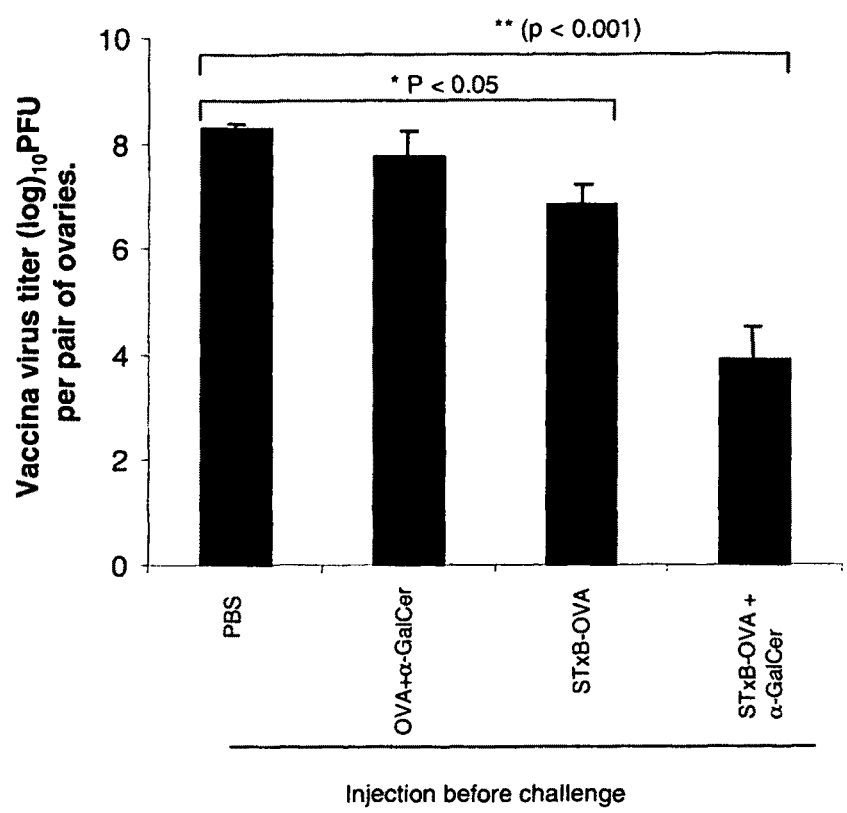

FIG. 7: STxB-OVA combined with α-GalCer induce antiviral protective immunity against a challenge with rVV-OVA. Mice (5 mice per group) were injected twice (d0 and d21) intraperitoneally (200 μl) either with B-OVA alone (0.05 nmol=5 μg), or B-OVA (0.05 nmol) combined with α-GalCer, or OVA (0.05 nmol) mixed with α-GalCer and control mice were injected with PBS. Similarly to the previous experiments, α-GalCer was not added during the second immunization. Eight days after the last injection mice were challenged intraperitoneally with 2.5×10$^6$ PFU recombinant vaccina virus (rVV-OVA, Westerns Reserve strains) expressing ovalbumin cDNA. After 4 days, ovaries were assayed for rVV titers by plaque assay on BHK 21 cells. Results represent mean of pfu from 6 mice per group. P values were calculated by a Student't test.

Figure 8:
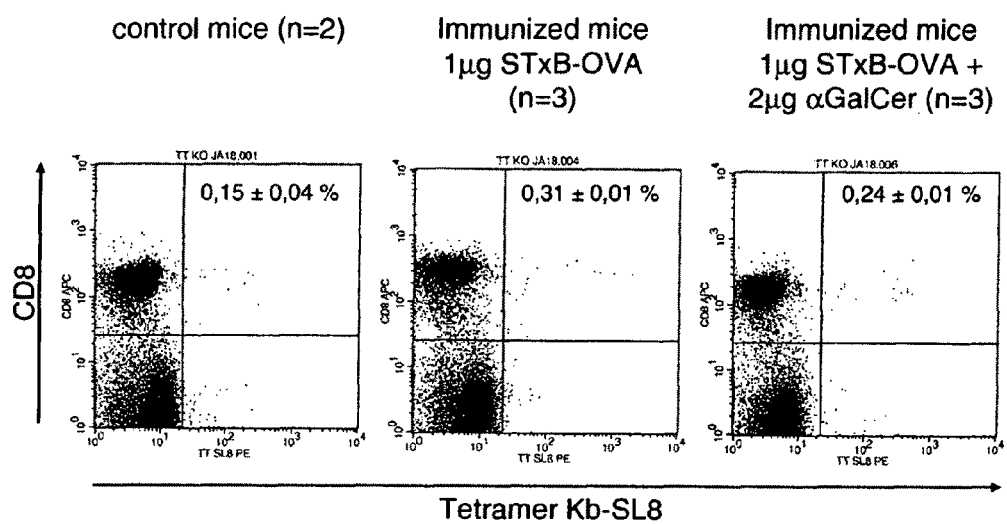

FIG. 8: No adjuvant effect of α-GalCer in mice deficient in NKT cells. Ja18$^{-/-}$ mice were immunized with STxB-OVA (1 μg) or STxB-OVA+α-GalCer (2 μg). 7 days after immunization, the spleens of immunized and non-immunized mice were harvested and stained with anti-CD8 antibody and OVA$_{257-264}$/K$^b$ tetramer.

Figure 9:
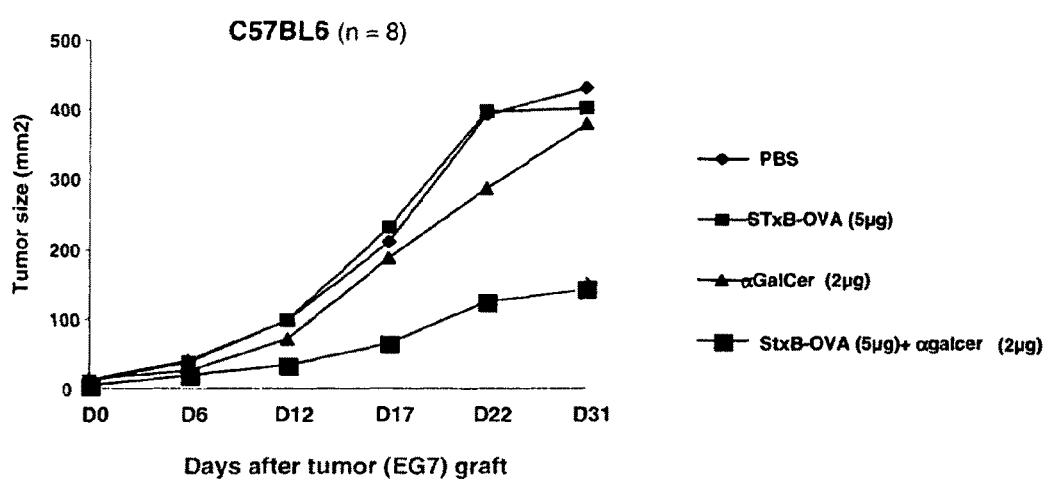

FIG. 9: Vaccination with αGalCer combined with STxB-Ova induces protection against established tumors. C57BL6 mice were grafted with EG7 tumor and three days after were vaccinated with PBS, STxB-OVA, α-GalCer, or STxB-OVA+α-GalCer.

DETAILED DESCRIPTION OF THE INVENTION

I. Definition

By "individual", it is meant mammal, in particular a human being.

By "effective amount", it is meant an amount sufficient to effect a beneficial or desired clinical result (e.g. improvement in clinical condition).

As used herein, "treatment" or "treating" generally refers to a clinical intervention in an attempt to alter the natural course of the individual or cell being treated, and may be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, preventing metastasis, lowering the rate of disease progression, ameliorating or palliating the disease state, and causing remission or improved prognosis.

The term "NKT cells" or "natural killer cell" is known in the art, and as used herein, refers to a T cell population that causes, stimulates or contributes to cytokine production, and/or in another embodiment, is cytotoxic. NKT cells are characterised by expression of both a T cell antigen receptor (TCR) and NK cell marker (i.e. NK1.1, a C-lectin-type NK receptor, DX5, Ly49 receptors in mice and NKR-P1A in human).

The term "Th1 cytokine" is known in the art and as used herein, refers to cytokine elicited by T helper cells as part of the adaptative immune response. Typically, Th1 cytokines are interleukin-2 or interferon-γ for example.

The term "Th2 cytokine" is known in the art, and as used herein, refers to cytokine elicited by T helper cells as part of the adaptative immune response. Typically, Th2 cytokine are interleukine-4 or interleukine-10, for example.

The term "dendritic cell" (DC) is known in the art, and as used herein, refers to antigen-presenting cells, which are capable of presenting antigen to T cells.

The term "mature dendritic cells" is known in the art, and as used herein, refers to a population of dendritic cells with diminished CD115, CD14, CD68 or CD32 expression, or a population of dendritic cells with enhanced CD86 expression, or a combination thereof. The term "stimulating an immune response" as used herein refers to the initiation of an immune response against an antigen of interest in an individual in which an immune response against said antigen has not already been initiated or refers to any improvement in an immune response that has already been mounted by an individual. It is to be understood that reference to the stimulation of the immune response may involve both the humoral and cell-mediated arms of the immune system. In one embodiment; stimulation of the immune response resulting in the stimulation of the humoral immune response may be reflected by an increase in antibody production and a TH2 cytokine profile (IL-4, Il-5, IL-6 . . . ) which can be determined by any means known in the art, such as for example by ELISA. In another embodiment, stimulation of the immune response resulting in the stimulation of the cell-mediated response may be reflected by an increase in IFN-γ or IL-12, or both, which may be similarly determined. In another embodiment, stimulating the immune response is associated with a change in cytokine expression. Such change may be readily measured by any means well-known in the art, such as ELISA, Western-Blot analysis, PCR analysis, and others.

The term "antigen" is known in the art, and as used herein, refers to any agent (protein, peptide, polysaccharide, glycoprotein, glycolipid, nucleic acid, or combination thereof), which elicits an immune response when introduced into a host and those which are able to elicit an immune response when complexed with the B subunit of Shiga toxin according to the invention. The term "antigen epitope" includes fragments of proteins capable of determining antigenicity. For example, antigens include proteins and other molecules which are specifically associated with surfaces of particular types of cancer cells, i.e. tumour cells. Alternatively, antigens may be associated with the surfaces or secretion products of micro-organisms or pathogens. The term "pathogen" is meant to include organisms that cause disorders, such disorders produced by one or more particular species of bacteria, viruses, fungi and protozoans which are disease-producing organisms. The term "antigen-related state" or "antigen-related condition" as used herein refers to micro-organism or pathogenic infections, allergen associated states or refers to the presence of a tumour.

The term "adjuvant" as used herein refers to a compound or a mixture that may be non-immunogenic when administered in the host alone, but that augments the host's immune response to an antigen when administered conjointly with that antigen.

The term "vaccine" as used herein refers to a composition that can be used to elicit protective immunity in a recipient. According to the present invention, a vaccine is a medicament.

II. The Present Invention

The present invention relates to a composition comprising a) a B subunit of Shiga toxin or a functional equivalent thereof which is able to bind the Gb3 receptor, complexed with an antigen and
b) at least one ligand of CD1 capable of stimulating NK T cells. The B subunit of Shiga toxin is secreted by *Shigella dysenteriae*. This homopentamer is responsible for toxin binding to and internalisation into target cells by interacting with the glycolipid Gb3 found in the plasma membrane of these cells. The B subunit of Shiga toxin has the sequence described in NA Strockbine et al. J Bacteriol 1988, 170, 1116-22.

A functional equivalent of the B subunit of Shiga toxin means a polypeptidic sequence having the capacity to bind specifically to the Gb3 receptor and/or to trigger an internalisation of an antigen and its presentation in an MHC class I restricted pathway, or both MHC class I and class II on the same antigen presenting cell.

Additionally, functional equivalents of the B subunit of Shiga toxin include homologous toxins, which are able to bind the Gb3 receptor, from other bacteria. For example, the B subunits of verotoxin-1 or verotoxin-2 from *E Coli* are also known to bind the Gb3 receptor. In the context of the present invention, the term "toxin" is intended to mean toxins that have been detoxified such that they are no longer toxic to humans, or a toxin subunit or fragment thereof that are substantially devoid of toxic activity in humans.

In one embodiment of the present invention, the functional equivalent of the B subunit of Shiga toxin has at least 50%, and preferably 60, 70, 80, 90 or 95%, amino acid identity to the B subunit of Shiga toxin.

The capacity of polypeptidic sequence to bind specifically to the Gb3 receptor may be evaluated by the following assay which is based on the method described by Tarrago-Trani (Protein extraction and purification 39, pp 170-176, 2004) and involves an affinity chromatography on a commercially available galabiose-linked agarose gel (Calbiochem). Galabiose (Galα1-4Gal) is the terminal carbohydrate portion of the oligosaccharide moiety of Gb3 and is thought to represent the minimal structure recognized by the B subunit of Shiga toxin. The protein of interest in PBS buffer (500 µl) is mixed with 100 µl of immobilized galabiose resin previously equilibrated with the same buffer, and incubated for 30 min to 1 hour at 4° C. on a rotating wheel. After a first centrifugation at 5000 rpm for 1 min, the pellet is washed twice with PBS. The bound material is then eluated twice by re-suspending the final pellet in 2×500 µl of 100 mM glycine pH 2.5. Samples corresponding to the flow-through, the pooled washes and the pooled eluates are then analysed by SDS Page, Coomassie staining and Western blotting.

CD1 molecules are a family of highly conserved antigen presenting proteins that are similar to in function to classical MHC molecules. CD1 proteins bind and display a variety of lipids and glycolipids to T lymphocytes. The five known isoforms are classified into two groups, group I (CD1a, CD1b, CD1c and CD1e in humans) and group II (CD1d in humans and mice).

In one embodiment, the ligand of CD1 present in the composition of the invention is a ligand of CD1d.

Certain ligands of CD1 molecule, when bound, stimulate NKT cells: for example they stimulate rapid Th1 and Th2 cytokine production by NKT cells.

In one embodiment of the present invention, said ligand induces Th1 and Th2 cytokine production, such as IL-4 and IFN-γ. Such cytokine production may be readily measured by any means well-known in the art, such as ELISA or by flow cytometry for example. In another embodiment, said ligand induces an increase in the expression of CD25, CD69 or Fas Ligand molecules, or an increase in the production of perforin. Such increase may be measured by any means well-known in the art, such as flow-cytometry for example.

In one embodiment of the present invention, said ligand of CD1 capable of stimulating NKT cells is a glycolipid, a phospholipid, a glycosphingolipid, a derivative or an analog thereof.

Glycosphingolipids are complex glycolipids which contain ceramide as an extra-lipid component. For example, Kirin Pharmaceutical in Japan identified several glycosphingolipids compounds, named agelasphins, from an extract of the Okinawan marine sponge, Agela mauritianus (Natori et al. Tetrahedron 1994, 50:2771-2784).

Other examples of glycolipid are: the lysosomal glycosphingolipid, isoglobotrihexosylceramide iGB3 (Zhou et al. Science 2004, 306:1786-1789); the disialoganglioside GD3 (Wu et al., J. Exp. Med. 2003, 198:173-181); the phosphatidylinositol PI (Gumperz et al. Immunity 2000, 12:211-221) and the phosphatidylethanolamine PE (Rauch et al. J. Bioch. Chem 2003, 278:47508-47515).

In one embodiment of the invention, said ligand is chosen from GD3, PE and PI.

In one embodiment of the present invention, said ligand is the sphingolipid as described in the U.S. Pat. No. 5,780,441, said sphingolipid having the following formula:

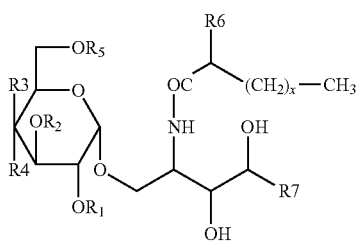

Wherein R1 represents H or

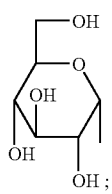

R2 represents H,

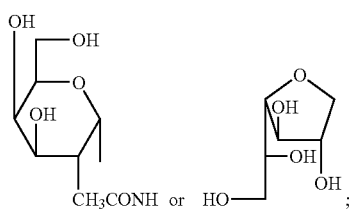

R3 and R6 represent H or OH, respectively;
R4 represents H, OH or

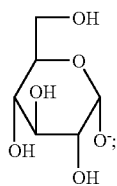

R5 represents H or

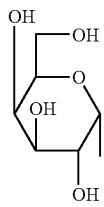

X denotes an integer from 19 to 23; and R7 represents any one of the following groups (a)-(g):
(a) —$(CH_2)_{11}$—$CH_3$,
(b) —$(CH_2)_{12}$—$CH_3$,
(c) —$(CH_2)_{13}$—$CH_3$,
(d) —$(CH_2)_{9}$—$CH(CH_3)_2$,
(e) —$(CH_2)_{10}$—$CH(CH_3)_2$,
(f) —$(CH_2)_{11}$—$CH(CH_3)_2$,
(g) —$(CH_2)_{11}$—$CH(CH_3)$—$C_2H_5$,
wherein at least one of R1, R2, R4 and R5 is a glycosyl moiety.

In another embodiment of the present invention, said ligand is an α-galactosylceramide as described in the U.S. Pat. No. 5,936,076, said α-galactosylceramide having the following formula:

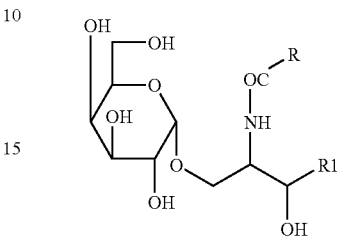

wherein R represents

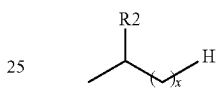

where R2 represents H or OH and X denotes an integer of 0-26 or R represents $(CH_2)_7CH=CH(CH_2)_7CH_3$ and R1 represents any one of the substituents defined by the following (a)-(e):
(a) —$CH_2(CH_2)_yCH_3$,
(b) —$CH(OH)(CH_2)_yCH_3$,
(c) —$CH(OH)(CH_2)_yCH(CH_3)_2$,
(d) —$CH=CH(CH_2)_yCH_3$, and
(e) —$CH(OH)(CH_2)_yCH(CH_3)CH_2CH_3$,
wherein Y denotes an integer of 5-17.

In another embodiment of the present invention, said ligand is an α-galactosylceramide as described in the U.S. Pat. No. 6,555,372, said α-galactosylceramide having the following formula:

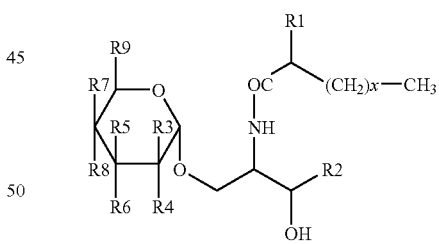

wherein R1 represents H or OH, X represents an integer between 7 and 27, R2 represents a substituent selected from the group consisting of the following (a) to (e) (wherein Y represents an integer between 5 and 17):
(a) —$CH_2(CH_2)_yCH_3$
(b) —$CH(OH)(CH_2)_yCH_3$
(c) —$CH(OH)(CH_2)_yCH(CH_2)_2$
(d) —$CH=CH(CH_2)_y(CH_3)$,
(e) —$CH(OH)(CH_2)_yCH(CH_3)CH_2CH_3$,
and R3 to R9 represent substituents as defined in any one of the following i) and ii):
i) when R3, R6 and R8 represent H, R4 represents H, OH, $NH_2$, $NHCOCH_3$, or a substituent selected from the group consisting of the following groups (A) to (D):

(A)
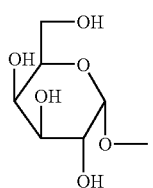

(B)
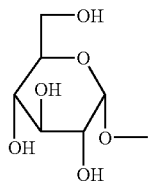

(C)
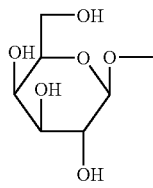

(D)
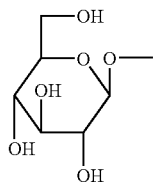

R5 represents OH or a substituent selected from the group consisting of the following groups (E) and (F):

(E)
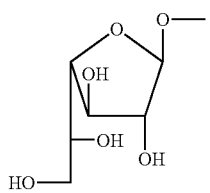

(F)
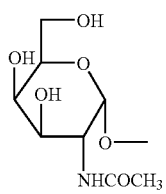

R7 represents OH or a substituent selected from the group consisting of the following groups (A) to (D):

(A)
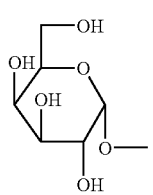

(B)
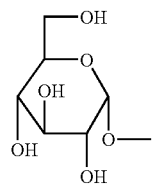

(C)
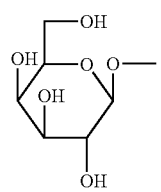

(D)
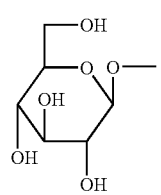

R9 represents H, CH$_3$, CH$_2$OH or a substituent selected from the group consisting of the following groups (A') to (D'):

(A')
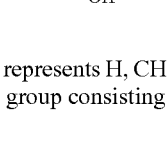

(B')
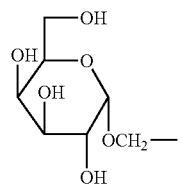

(C')
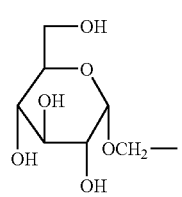

(D')
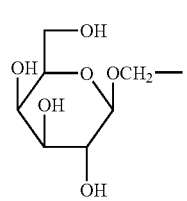

ii) when R3, R6 and R7 represent H, R4 represents H, OH, NH$_2$, NHCOCH$_3$, or substituent selected from the group consisting of the following groups (A) to (D):

(A)
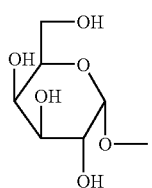

(B)
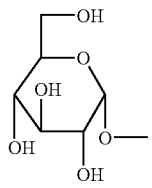

(C)
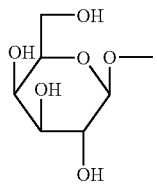

(D)
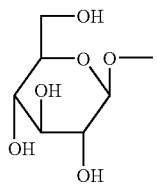

R5 represents OH or a substituent selected from the group consisting of groups (E) and (F):

(E)
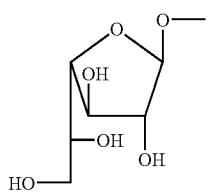

(F)
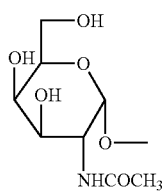

R8 represents OH or a substituent selected from the group consisting of the following groups (A) to (D):

(A)
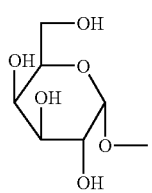

(B)
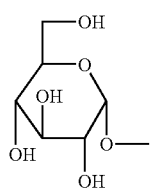

(C)
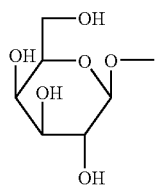

(D)
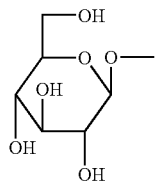

R9 represents H, CH3, CH2OH or a substituent selected from the group consisting of the following groups (A') to (D'):

(A')
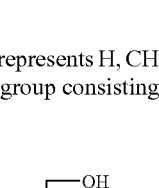

(B')
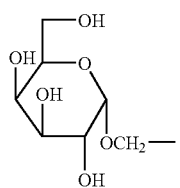

(C')
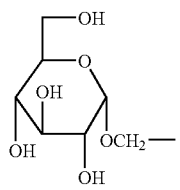

(D')
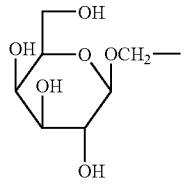

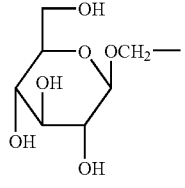

or a salt or solvate thereof.

In a preferred embodiment of the present invention; said ligand is the compound KRN7000, having the following formula: (2S,3S,4S)-1-(α-D-galactopyranosyloxy)-2-hexacosanoymamino-3,4-octadecanediol.

In another embodiment of the present invention, said ligand is a glycolipid derivative as described in the patent application US2002/0032158, said glycolipid derivative having the following formula:

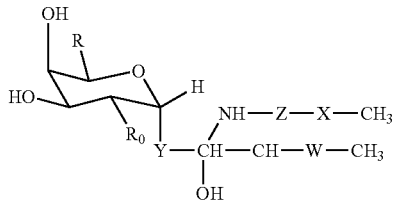

wherein W represents carbone chain from 9 to 17 which containing double bond or hydroxy group occasionally; X represents carbone chain from 11 to 25 which containing double bond or hydroxy group occasionally; Y represents —(CH$_2$)$_a$—CH=CH—(CH$_2$)$_{a'}$—, —(CH$_2$)$_a$-(a, a' denotes an integer of 0-5 and a+a' is 5 and under.), —S(O)$_{0-2}$CH$_2$—, —NHCH$_2$; Z represents —CO—, —SO$_2$; R represents —CH$_2$OH, —CO$_2$H, —CH$_2$OCH$_2$CO$_2$H, —CH$_2$OSO$_3$H; R$_0$ represents —OH, —NH$_2$, —NHAc.

In another embodiment of the present invention, said ligand is a glycosylceramide as described in the patent application US2003/0157135, said glycosylceramide having the following formula:

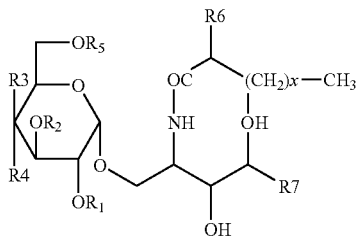

wherein R1, R2 and R5 represent H or a specific monosaccharide; R3 and R6 represent H or OH, respectively; R4 represents H, OH or a specific monosaccharide; X denotes an integer from 1 to 23; R7 represents any one of the following groups (a)-(g):
(a) —(CH$_2$)$_{11}$—CH$_3$,
(b) —(CH$_2$)$_{12}$—CH$_3$,
(c) —(CH$_2$)$_{13}$—CH$_3$,
(d) —(CH$_2$)$_9$—CH(CH$_3$)$_2$,
(e) —(CH$_2$)$_{10}$—CH(CH$_3$)$_2$,
(f) —(CH$_2$)$_{11}$—CH(CH$_3$)$_2$,
(g) —(CH$_2$)$_{11}$—CH(CH$_3$)—C$_2$H$_5$.

In a preferred embodiment, said ligand is a glycosylceramide or an analog or a derivative thereof.

In a more preferred embodiment, said ligand is selected from the group consisting of α-galactosylceramide (α-GalCer), α-glucosylceramide (α-GlcCer), Galα1-6Galα1-1'Cer, Galα1-6Glcα1-1' Cer, Galα1-2Galα1-1'Cer, Galβ1-3Galα1-1'Cer or a derivative thereof, preferably a C-glycoside derivative thereof, more preferably a C-glycoside derivative of α-GalCer.

In another preferred embodiment, said ligand has the following formula (2S,3S,4R)-1-O-(α-D-galactopyranosyl)-2-(N-hexa-cosanoylamino)-1,3,4-octadecanetriol.

In another embodiment, said ligand has the following formula (2S,3S,4S)-1-O-(α-D-galactopyranosyloxy)-2-hexacosanolamino-3,4-octadecanediol (KRN7000).

In another embodiment, said ligand is an α-GalCer analog, called α-C-GalCer, as described in the patent application US2004/0127429, said ligand having the following formula:

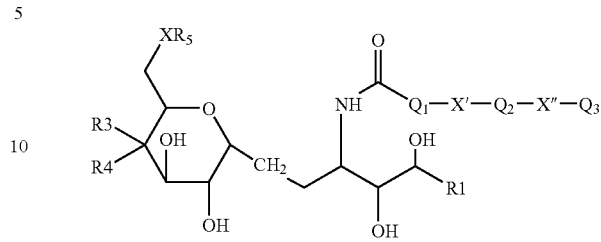

wherein X is O or NH; R1 is selected from the group consisting of —(CH$_2$)$_{11}$CH$_3$, —(CH$_2$)$_{12}$CH$_3$, —(CH$_2$)$_{13}$CH$_3$, —(CH$_2$)$_9$CH(CH$_3$)$_2$, —(CH$_2$)$_{10}$CH(CH$_3$)$_2$, —(CH$_2$)$_{11}$CH(CH$_3$)$_2$ and (CH$_2$)$_{11}$CH(CH$_2$)—C$_2$H$_5$;

R3 is OH or a monosaccharide and R4 is hydrogen, or R3 is hydrogen and R4 is OH or a monosaccharide;

R5 is hydrogen or a monosaccharide;

Q$_1$ is optionally present and is a C$_{1-10}$ straight or branched chain alkylene, alkenylene, or alkynylene;

X' is optionally present and is O, S or NR$^8$;

Q$_2$ is optionally present and is a C$_{1-10}$ straight or branched chain alkylene, alkenylene or alkynylene;

X" is optionally present and is O, S or NR$^8$;

Q$_3$ is a straight or branched chain C$_{1-10}$ alkylene, alkenylene or alkynylene, or is hydrogen, wherein each Q$^1$, Q$^2$ or Q$^3$ is optionally substituted with hydroxyl, halogen, cyano, nitro, SO$_2$ NHR$^8$, or C(=O)—R$^9$; and wherein R8 is hydrogen, C$_{1-5}$ alkyl, C$_{1-5}$ alkoxy, halogen, cyano, nitro, SO$_2$ or C(=O)—R$^9$;

R9 is hydrogen, C$_{1-5}$ alkyl, C$_{1-5}$ alkoxy or NHR$^{10}$;

R10 is hydrogen, C$_{1-5}$ alkyl or C$_{1-5}$ alkoxy;

and a pharmaceutically acceptable salt or ester thereof.

In another embodiment, said ligand is PBS-57, which structure was described by Liu et al. Journal of Immunological Methods, 312 (2006) 34-39.

In another embodiment, said ligand is a C-glycolipid, as described in the patent application US2005/0222048, having the following formula:

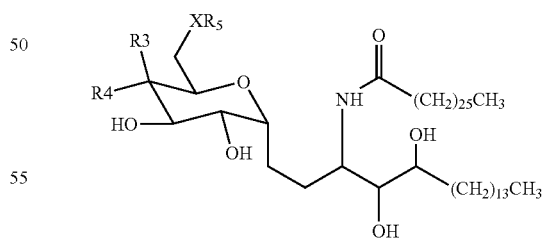

wherein X is O or NH; R3 is OH or a monosaccharide and R4 is hydrogen, or R3 is hydrogen and R4 is OH or a monosaccharide; R5 is hydrogen or a monosaccharide; and pharmaceutically acceptable salts or esters thereof.

In another embodiment of the present invention, said ligand is an immunogenic compound as described in the patent application US2006/0211856, having the following formula:

![Chemical structure showing a pyranose ring with substituents HO, R, R2O, R5 linked via O-CH2 to a carbon bearing OH, R3', R3, and an amide group HN-C(=O)-CHR4'-R4]

wherein, R=COOR1 or CH$_2$OR1;
R1=H or an alkyl group;
R2=H or SO$_3^-$;
R3=H or OH;
R$_3$'=H or OH;
R4=H, unsaturated or saturated, alkyl group;
R$_4$'=H, unsaturated or saturated, alkyl group; and
R5=OH, acetamido or a halogen atom;
or a pharmaceutically acceptable salt thereof,
wherein if R=CH$_2$OR$_1$, R$_2$=H, R$_3$' is OH and R$_3$ is H, then R$_5$=acetamido, halogen atom or OH in an axial position or R$_4$=H, unsaturated or saturated, alkyl chain having 9 carbon atoms or fewer, or R$_4$=H, unsaturated or saturated, alkyl chain having 20 carbon atoms or fewer.

In a preferred embodiment of the present invention, said ligand is selected from 3-O-sulfo-α-GalCer, β-GalCer, an OCH compound, α-C-GalCer.

The OCH compound is described in the patent application US2006/0148723, and has the following formula:

$$R1-O-CH_2-\underset{\underset{NH-CO-\underset{\underset{R2}{|}}{CH}-(CH_2)x CH_3}{|}}{CH}-CH(OH)-R3-(CH_2)y(CH(CH_3))_2-CH(R_4)_2$$

wherein, R1 is an aldopyranose group, R2 is a hydrogen atom or a hydroxyl group, R3 is —CH$_2$—, —CH(OH)—CH$_2$— or —CH=CH—, R4 is a hydrogen atom or CH$_3$, x is 0-35, y and z represent integers satisfying y+z=0-3.

α-C-GalCer has been described above. 3-O-sulfo-α-GalCer is a sulfatide variant of α-GalCer and has been described in the article Wu et al. (Wu et al. PNAS 2005, 102:1352-1356).

In another embodiment of the present invention, said ligand is a microbe derived glycolipid.

In a preferred embodiment, said ligand is
a *Sphingomonas* species-derived glycosphingolipid selected in the group consisting of GSL-1 and GSL'1 or
a *Borrelia* species derived glycolipid selected from the group consisting of BbGL-I and BbGL-II or
a *Mycobacteria* species derived phosphoglycolipid PIM.

In one embodiment of the present invention, the composition of the invention comprises the B subunit of Shiga toxin, or the functional equivalent thereof, present in a universal polypeptidic carrier having the formula STxB-Z(n)-Cys, wherein
—STxB is the Shiga Toxin B subunit or a functional equivalent thereof,
Z is an amino-acid devoided of sulfydryl group, n being 0, 1 or a polypeptide,
Cys is the amino-acid Cysteine.

This universal carrier has been described in the patent application WO02/060937.

The STxB moiety of the universal carrier has the sequence described in NA Strockbine et al. J Bacteriol 1988, 170, 1116-22, or a functional equivalent thereof.

In a preferred embodiment, n is 0 and the universal carrier has the following sequence (SEQ ID NO:1):

COOH-MKKTLLIAASLSFFSASALATPDCVTGKVEYTKYNDDDTFTVKVG
    DKELFTNRWNLQSLLLSAQITGMTVTIKTNACHNGGGFSEVIFRC-NH2.

As a matter of fact, if the Z linker is too long, i.e. when n is equal or greater than 2, some internal disulfide bridges might occur, and prevent either the binding of STxB to Gb3 receptor.

In another embodiment of the invention, the antigen is to be targeted to antigen presentating cells. Such cells are selected in a group comprising T lymphocytes, dendritic cells, macrophages, Langerhans cells and the like.

The coupling approaches for covalent binding of an antigen to STxB-Z (n)-Cys can be any method or processes described or carried out by a skilled person.

A first method that can be embodied is the use of SPDP hetero-bi-functional cross-linker described par Carlsson et al (5). However, SPDP is capable of being cleavable by serumthiolases that is a cause of decreasing the yield of the reaction.

A second method for covalent coupling of STxB-Z (n)-Cys peptides with an antigen is to produce bromoacetyl or maleimide functions on the latter as described by P. Schelte et al (4).

Briefly, the antigen is chemically activated with bromoacetate anhydride or by a maleimide group respectively. In appropriate reaction conditions (pH, temperature, incubation times), these groups are eliminated by cis-elimination, yielding respectively to —S—S, —S—CH2-, to —S—CO— or S—NH-covalent linkages.

As an example, the antigen to be coupled to the —SH moiety the C-terminal Cysteine of the universal carrier, has its N-terminus activated with bromoacetic anhydride following the reaction scheme:

Br—CH2-CO—O—CO—CH2-Br+NH2-
        antigen=>Br—CH2-CO—NH-antigen+Br—
        CH2-COOH The Bromoacetyl function has high chemoselectivity for peptide thiol groups and the activated peptide can be reacted with STxB-Cys as follows:

STxB-Cys-SH+Br—CH2-CO—NH-antigen=>STxB-
        Cys-S—CH2-CO—NH-antigen+HBr

The resulting thioether-linkage is stable to hydrolysis.

Another method for coupling an antigen to the universal carrier of the invention is to use MBS (m-Maleimidobenzoyl-N— hydroxysuccinimide ester).

This coupling allows the transport and processing of large molecules such antigenic proteins or glycoproteins through MHC class I and/or MHC class 11 pathways.

Thus, in one embodiment of the invention, the antigen is covalently linked to the —S residue of the universal carrier by a —S—S, or —S—CO, or S—CH$_2$, or —S—NH linkage.

In another embodiment, the universal carrier according to the present invention can be operably linked directly through a covalent binding or indirectly through a linker.

The term "indirect binding" means that the universal carrier is covalently linked through the sulfhydryl moiety of the C-terminal Cysteine to a linker, said linker being operably linked to an antigen to be internalized into Gb3 receptor bearing cells.

This linkage might be a covalent binding or a non-covalent binding, provided that the affinity between the linker and the antigen is higher than $10^{-9}$ mole/l.

Thus, the universal carrier is covalently linked to an oligopeptide or a polypeptide by a —S—S, or —S—CO, or S—CH$_2$, or —S—NH linkage, and the antigen to be targeted is operably linked to the said oligopeptide or polypeptide. In a preferred embodiment, the universal carrier is covalently linked to a poly-lysine oligopeptide and the antigen to be targeted is operably linked to the said poly-lysine moiety.

In one embodiment of the present invention, the antigen complexed to the B subunit of Shiga toxin is a tumor antigen, a viral antigen or a bacterial antigen.

In a preferred embodiment, the antigen is selected such that it provides immunity against intracellular pathogens such as HIV, tuberculosis, *Chlamydia*, HBV, HCV and influenza. Preferably, the antigen is derived from HIV (such as gag or fragments thereof, such as p24, tat, nef, envelope such as gp120 or gp160, or fragments of any of these), human herpes viruses, such as gD or derivatives thereof or Immediate Early protein such as ICP27 from HSV1 or HSV2, cytomegalovirus ((esp Human) (such as gB or derivatives thereof), Rotaviral antigen, Epstein Barr virus (such as gp350 or derivatives thereof), Varicella Zoster Virus (such as gpl, 11 and IE63), or from a hepatitis virus such as hepatitis B virus (for example Hepatitis B Surface antigen or a derivative thereof), or antigens from hepatitis A virus, hepatitis C virus and hepatitis E virus, or from other viral pathogens, such as paramyxoviruses: Respiratory Syncytial virus (such as F G and N proteins or derivatives thereof), parainfluenza virus, measles virus, mumps virus, human papilloma viruses (for example HPV 6, 11, 16, 18,) flaviviruses (e.g. Yellow Fever Virus, Dengue Virus, Tick-borne encephalitis virus, Japanese Encephalitis Virus) or Influenza virus purified or recombinant proteins thereof, such as HA, NP, NA, or M proteins, or combinations thereof), or derived from bacterial pathogens such as *Neisseria* spp, including *N. gonorrhea* and *N. meningitidis* (for example, transferrin-binding proteins, lactoferrin binding proteins, PilC, adhesins); *S. pyogenes* (for example M proteins or fragments thereof, C5A protease,), *S. agalactiae, S. mutans; H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human *Granulocytic Ehrlichiosis; Rickettsia* spp, including *R. rickettsii; Chlamydia* spp., including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans*.

Other preferred specific antigens for *M. tuberculosis* are for example Tb Ra12, Tb H9, Tb Ra35, Tb38-1, Erd 14, DPV, MTI, MSL, mTTC2 and hTCC1 (WO 99/51748).

Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748).

Most preferred antigens for *Chlamydia* include for example the High Molecular Weight Protein (HMW) (WO 99/17741), ORF3 (EP 366 412), and putative membrane proteins (Pmps). Other *Chlamydia* antigens of the vaccine formulation can be selected from the group described in WO 99/28475.

Preferred bacterial antigens are derived from *Streptococcus* spp, including *S. pneumoniae* (for example, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other preferred bacterial vaccines comprise antigens derived from *Haemophilus* spp., including *H. influenzae* typeB, non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Derivatives of Hepatitis B Surface antigen are well known in the art and include, inter alia, those PreS1, PreS2 S antigens set forth described in European Patent applications EP-A-414 374; EP-A-0304 578, and EP 198-474.

In another embodiment, the antigen is derived from the Human Papilloma Virus (HPV) considered to be responsible for genital warts (HPV 6 or HPV 11 and others), and the HPV viruses responsible for cervical cancer (HPV16, HPV18 and others). Particularly preferred forms of genital wart prophylactic, or therapeutic, vaccine comprise L1 protein, and fusion proteins comprising one or more antigens selected from the HPV proteins E1, E2, E5, E6, E7, L1, and L2. The most preferred forms of fusion protein are: L2E7 as disclosed in WO 96/26277, and proteinD (⅓)-E7 disclosed in WO99/10375. A preferred HPV cervical infection or cancer, prophylaxis or therapeutic vaccine, composition may comprise HPV 16 or 18 antigens. Particularly preferred HPV 16 antigens comprise the early proteins E6 or E7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such vaccine may optionally contain either or both E6 and E7 proteins from HPV 18, preferably in the form of a Protein D-E6 or Protein D-E7 fusion protein or Protein D E6/E7 fusion protein.

Antigens may also derived from parasites that cause Malaria, for example, antigens from Plasmodia falciparum including circumsporozoite protein (CS protein), RTS, S, MSP1, MSP3, LSA1, LSA3, AMA1 and TRAP. RTS is a hybrid protein comprising substantially all the C-terminal portion of the circumsporozoite (CS) protein of P. falciparum linked via four amino acids of the preS2 portion of Hepatitis B surface antigen to the surface (S) antigen of hepatitis B virus. Its full structure is disclosed in International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS, S. TRAP antigens are described in International Patent Application No. PCT/GB89/00895, published under WO 90/01496. Plasmodia antigens that are likely candidates to be components of a multistage Malaria vaccine are P. falciparum MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp.

Examples of tumor antigens include MAGE 1 and MAGE 3 or other MAGE antigens (for the treatment of melanoma), PRAME, GAGE, or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p 293. Indeed these antigens are expressed in a wide range of tumour types such as melanoma, lung carcinoma, sarcoma and bladder carcinoma. Other tumour-specific antigens include, but are not restricted to tumour-specific gangliosides, Prostate specific antigen (PSA) or Her-2/neu, KSA (GA733), PAP, mammaglobin, MUC-1, carcinoembryonic antigen (CEA). Other tumour-associated antigen comprise Prostate-specific membrane antigen (PSMA), Prostate Stem Cell Antigen (PSCA), tyrosinase, survivin, NY-ES01, prostase, PS108 (WO 98/50567), RAGE, LAGE, HAGE. Additionally said antigen may be a self peptide hormone such as whole length Gonadotrophin hormone releasing hormone (GnRH, WO 95/20600), a short 10 amino acid long peptide, useful in the treatment of many cancers, or in immunocastration.

In a preferred embodiment of the invention, the antigen complexed to the B subunit of Shiga toxin is chosen among E6, E7, antigens from the Mage family, Her2/neu, EGFRVIII, survivin, telomerase, WT1 and ESAT6.

In one embodiment of the present invention, the composition above described further comprises a pharmaceutically acceptable carrier.

In one embodiment, the compositions of the present invention are formulated as oral or parenteral dosage forms, such as uncoated tablets, coated tablets, pills, capsules, powders, granulates, dispersions or suspensions. In another embodiment, the compositions of the present invention are formulated for intravenous administration. In another embodiment, the compounds of the present invention are formulated in ointment, cream or gel form for transdermal administration. In another embodiment, the compounds of the present invention are formulated as an aerosol or spray for nasal application. In another embodiment, the compositions of the present invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents Parenteral and intravenous forms should also include minerals and other materials to make them compatible with the type of injection or delivery system chosen. Of course, other excipients may also be used.

There is also an object of the present invention to provide a medicament comprising the composition of the invention.

Another object of the present invention is to provide a vaccine comprising said composition.

The amount of antigen in each vaccine dose is selected as an amount which induces an immunoprotective response without significant, adverse side effects in typical vaccines.

Generally, it is expected that each human dose will comprise 0.1-1000 µg of antigen, preferably 0.1-500 µg, preferably 0.1-100 µg, most preferably 0.1 to 50 µg. An optimal amount for a particular vaccine can be ascertained by standard studies involving observation of appropriate immune responses in vaccinated subjects. Following an initial vaccination, subjects may receive one or several booster immunisations adequately spaced. Such a vaccine formulation may be applied to a mucosal surface of a mammal in either a priming or a boosting vaccination regime; or alternatively be administered systemically, for example via the transdermal, subcutaneous or intramuscular routes. Intramuscular administration is preferred.

Another object of the present invention is a pharmaceutical kit comprising:
a) a first container comprising a B subunit of Shiga toxin or a functional equivalent thereof which is able to bind the Gb3 receptor, complexed with an antigen as described above and
b) at least a second container comprising at least one ligand of CD1 capable of stimulating NK T cells as described above.

Preferably, said ligand of CD1 is a ligand of CD1d. More preferably, said ligand is chosen among all ligands cited above.

Another object of the present invention is to provide a process for the preparation of said composition wherein the B subunit of Shiga toxin or a functional equivalent thereof which is able to bind the Gb3 receptor, complexed with an antigen is mixed with at least one ligand of CD1 capable of stimulating NK T cells.

The formulations of the present invention may be used for both prophylactic and therapeutic purposes.

A further object of the present invention is therefore the use of the composition as described above for the manufacture of a pharmaceutical composition or a medicament, including a vaccine, for treating an antigen-related condition in an individual, said antigen-related condition being a tumor or an infection.

In a preferred embodiment, the composition as described above is used for the manufacture of a pharmaceutical composition or medicament, including a vaccine, for treating cancer.

In one embodiment, the present invention relates to the use of said composition for treating an antigen-related state in an individual in need thereof. Said pharmaceutical composition or medicament is to be administrated to the individual in a therapeutically effective amount for stimulating an immune response against the antigen in said individual, thereby treating said antigen-related condition in said individual.

In another embodiment, the present invention relates to the use of said composition for treating an antigen-related condition in an individual in need thereof, wherein the composition is to be administered in combination with thalidomide or an analog thereof, preferably lenalidomide.

Indeed, it was shown that lenalidomide and its analogues enhance CD1d-mediated presentation of glycolipid antigens, and therefore enhance antigen-specific activation of NKT cells.

In another embodiment, the present invention relates to the use of the kit as described above, wherein at least one ligand of CD1 capable of stimulating NKT cells is to be administrated before, simultaneously or after the B subunit of Shiga toxin or a functional equivalent thereof which is able to bind the Gb3 receptor, complexed with an antigen. According to the invention, the use of said composition allows the delivery of the antigen into a Gb3 receptor expression cells.

According to the invention, the stimulation of the immune response induced by the use of the composition of the invention comprises stimulating dendritic cells.

According to the invention, the stimulation of the immune response induced by the use of the composition of the invention comprises eliciting an antigen specific CD8+ response.

EXAMPLES

In the following description, all molecular biology experiments for which no detailed protocol is given are performed according to standard protocol.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

I. Material and Methods.

Mice

Female C57BL/6 (H-$2^b$) mice were purchased from Charles River Laboratories (L'Arbresle, France). OT-I TCR transgenic (TG) mice specific for the ovalbumin (OVA) peptide (SIINFEKL) in the context of H-$2K^b$ were provided by Dr C Leclerc (Institut Pasteur). OVA-TG mice were obtained from Dr P. Shrikant (Roswell Park Cancer Institute, Buffalo, N.Y.) with the permission of Dr M. K Jenkins (University of Minnesota). These mice present the C57BL/6 background and express low levels of the membrane-associated form of chicken ovalbumin protein (OVA) in most actin-expressing cells. Mice were kept under specific pathogen-free conditions and were used between 6 and 8 weeks of age according to institutional guidelines.

Chemical Reagents (Recombinant Proteins, Peptides, Adjuvant)

Purified chicken ovalbumin (OVA) (grade V) was purchased from Sigma (St Quentin Fallavier, France). Synthetic OVA-derived peptide $OVA_{257-264}$ (SIINFEKL) and HPV16-E7 derived peptide $E7_{49-57}$ (RAHYNIVTF) or $E7_{43-57}$ (GQAEPDRAHYNIVTF) were obtained from NeoMPS (Strasbourg, France) and stored in PBS.

STxB-OVA was obtained by chemical coupling, as previously described (Haicheur, N., et al. 2003. *Int Immunol* 15:1-11). Briefly, OVA was first activated via amino groups on lysine side chains using the heterobifunctional cross-linker MBS (Pierce, Rockford, Ill.). Activated OVA was then reacted with STxB-Cys, and the reaction product was purified by gel filtration and immunoaffinity chromatography. STxB-$E7_{43-57}$ was produced using a chemical coupling between the N-bromoacetylated $E7_{43-57}$ peptide and the sulfhydril group of the STxB-Cys recombinant protein as previously described (Mallard, F. et al. 2003. *Methods Mol Med* 73:209-220). Removal of contaminating LPS was carried out using Acticlean Etox columns (Biotech-IgG, Kobenhavn, Denmark). After purification, endotoxin concentrations determined by the *Limulus* assay test (Biowhittaker, Walkersville, Md.) were <0.5 EU/mg.

The iNKT cell ligand α-GalCer (KRN7000) was kindly supplied by Kirin Brewery Co (Japan). Poly (I:C) and incomplete Freund's adjuvant (IFA) were purchased from Sigma (St Quentin-Fallavier, France). CpG ODN 1826 was purchased from Proligo (Paris, France).

IFNα was kindly provided by Ion Gresser (Inserm, France)

Cells

The mouse thymoma cell line EL4 (H-$2^b$) was kindly provided by K. Rock (University of Massachusetts Medical School, Worcester, Mass.) and P Jeannin (Angers University Hospital, France)

ELISPOT Assay

The functionality of the anti-$OVA_{257-264}/K^b$ $CD8^+$ T cells induced after injection of STxB-OVA was determined by ELISPOT according to the manufacturer's recommendations (Diaclone, Besancon, France). Briefly, $10^5$ $CD8^+$ T cells were transferred to anti-mouse IFNγ mAb precoated plates and cultured for 18 hours at 37° C. with $10^5$ EL4 cells previously pulsed (or not) with the $OVA_{257-264}$ peptide and fixed with 1% paraformaldehyde. After washings, the plates were further incubated with biotinylated anti-mouse IFNγ mAb. Finally, the plates were washed and incubated for 30 min at 37° C. with alkaline phosphatase-labeled streptavidin. Spots were developed by adding 5-bromo-4-chloro-3-indolyl-phosphatase/nitroblue tetrazolium. Positive controls included cells stimulated with phorbol myristate acetate (100 ng/ml, Sigma) and ionomycin (500 ng/ml, Sigma). Controls consisted of cells cultured in the absence of the $OVA_{257-264}$ peptide. IFN γ spot-forming cells (SFCs) were counted on a KS-ELISPOT system (Carl Zeiss, Munich, Germany).

Cytotoxicity Assay

Cytotoxicity was assessed on $^{51}Cr$-labeled target cells as previously described (Haicheur, N., et al. 2000. *J Immunol* 165:3301-3308)

Flow-Cytometry

To detect anti-$OVA_{257-264}/K^b$ or anti-$E7_{49-57}/D^b$ specific $CD8^+$ T cells, the cells were stained with $OVA_{257-264}/K^b$ or $E7_{49-57}/D^b$ tetramer according to the manufacturer's recommendations (Beckman-Coulter Immunomics, Marseilles, France). Briefly, cells were incubated with PE-labeled tetramer (45 min at 4° C. in the dark). After incubation and washes, labeled anti-CD8 mAbs (ebioscience, San Diego, Calif.) were used to phenotype the positive tetramer CD8$^+$T cells. Irrelevant tetramers recognizing a VSV derived peptide in the context of K$^b$ or D$^b$ molecules were used in each experiment. Naive non immunized mice were also included as control for these experiments.

Proliferation Assay to Detect Specific Anti-Ova Cd4$^+$T Cells

CD4$^+$T cells were purified from spleen and labeled with CFSE (Molecular Probes, Eugene, Oreg.), used at 0.5 μM for 30 min at 20° C. Labeling was stopped by repeated washing with ice-cold PBS supplemented with 5% FCS. Cells were then incubated with T cell depleted splenocytes as APC pulsed or not with free ovalbumin protein and cocultured for 5 days in AIM V serum free medium. Proliferation in absence of APC sensitization were subtracted as background from values obtained after ovalbumin pulsing.

Ex Vivo Cross-Presentation Assay

Anti-OVA specific CD8$^+$T cells derived from OT-1 mice were labeled with CFSE. CD11c$^+$ enriched dendritic cells ($10^6$) isolated as described (37) from mice vaccinated with various vaccine formulations were co-cultured with OT-1 cells ($5.10^5$) for 72 hours. Dilution of CFSE detected by FACS analysis was considered to be an indicator of OT-1 cell proliferation after antigen recognition.

Serological Analysis

It was performed as previously described (Haicheur, N., F. et al. 2003. *Int Immunol* 15:1-11).

Anti-Viral Protection Experiments

C57BL/6 mice (5 mice per group) were injected twice (d0 and d21) intraperitoneally (200 μl) with different vaccine formulations and control mice were injected with PBS. Eight days after the last injection, mice were challenged intraperitoneally with $2.5 \times 10^6$ PFU recombinant vaccina virus (rVV, Westerns Reserve strains) expressing either the ovalbumin or the HBx cDNA derived from Hepatitis B virus kindly provided, by Dr N Etchart (INSERM, Lyon) and Dr Lone Yu Chun (Institut Pasteur), respectively. After 4 days, the ovaries of the mice were harvested and homogenized with a mechanical tissue grinder. The homogenates were clarified by centrifugation at 4,000 g for 10 min, and the number of rVV PFU in the resultant supernatant was enumerated by infecting BHK 21 cell monolayers with 10-fold serial dilutions of these fluids and plaques were counted after 2 days in culture at 37° C. in a 5% $CO_2$ environment as previously described (52).

Results

α-GalCer Increased the Efficiency of STxB Coupled to Antigen to Induce Specific CTL.

A first series of experiments tested the ability of various well defined adjuvants to increase the efficiency of STxB-OVA to trigger a specific CTL response.

Figure 2:
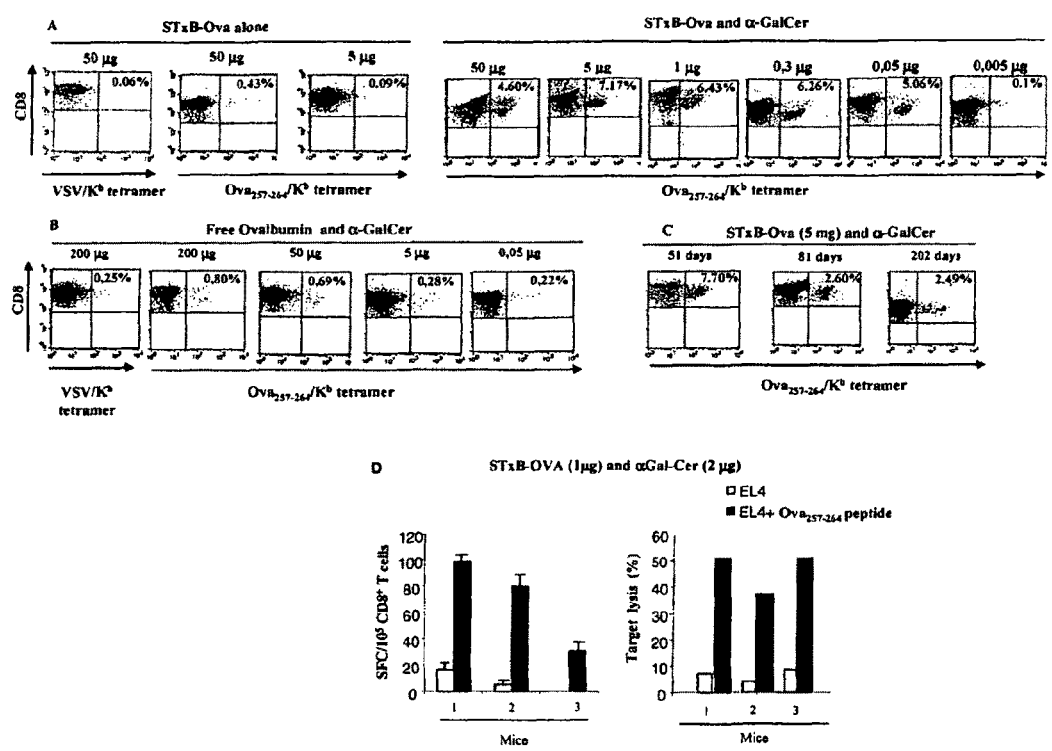

As previously reported, when mice were immunized twice with the STxB-OVA conjugate (50 μg) alone, an induction of anti-OVA$_{257-264}$ CD8$^+$T cells corresponding to 0.4% of CD8$^+$T cells was demonstrated (FIGS. 1 and 2A). Except for IFA, all other adjuvants (IFNα, Poly (I:C), CpG and α-GalCer) combined with STxB-OVA significantly enhanced the frequency of anti-OVA$_{257-264}$ CD8$^+$T cells. However, whereas, IFNα, Poly (I:C) and CpG led to a modest increase of anti-OVA$_{257-264}$ CD8$^+$T cells detected by specific tetramer not exceeding 1% of total CD8$^+$T cells, the glycolipid α-GalCer elicited a dramatic increase of the percent of specific anti-OVA CTL (FIG. 1). Indeed, after two immunizations with STxB-OVA and α-GalCer, 4.6% of CD8$^+$T cells stained positively with OVA$_{257-264}$/K$^b$ tetramer directly ex vivo without any in vitro restimulation step (FIG. 1). We therefore focused on analysis of this synergy between STxB and α-GalCer. Since previous studies reported that repeated administration of α-GalCer may lead to anergy and TH2 polarization (53-55) and no difference was observed when α-GalCer was injected during both the first and second immunizations or only at priming, we only combined this adjuvant and STxB-OVA during the first immunization.

When different doses of the STxB-OVA conjugate were mixed with α-GalCer, this adjuvant was found to significantly induce the anti-OVA$_{257-264}$ CTL response even at very low doses of antigen (50 ng STxB-OVA corresponding to 25 ng of equivalent ovalbumin antigen)(FIG. 2A). In contrast, free ovalbumin even at high doses (200 μg) combined with α-GalCer elicited a low frequency of anti-OVA$_{257-264}$ CTL not exceeding 1% of total CD8$^+$T cells (FIG. 2B) compared to 5-7% of anti-OVA$_{257-264}$ specific CTL when ovalbumin was coupled to STxB and combined with α-GalCer. In addition, no significant induction of anti-OVA$_{257-264}$ CD8$^+$T cells was shown when less than 50 μg of OVA was added to α-GalCer or when OVA alone was used for immunization (FIG. 2B). The other adjuvants (IFNα, Poly (I:C), CpG) did not allow this priming of CTL when a low dose of STxB-OVA conjugate was used reinforcing the significance of the synergy between STxB and α-GalCer (data not shown).

The specific anti-OVA$_{257-264}$ CD8$^+$T cells induced by the combination of α-GalCer and the STxB-OVA conjugate were long-lasting as 2.49% of CD8$^+$T cells stained positively with OVA$_{257-264}$/K$^b$ tetramer directly ex vivo 202 days after the first immunization (FIG. 2C).

Since tetramer analysis does not discriminate between anergic and functional CD8$^+$T cells, two functional tests, an Elispot assay and a cytotoxic assay on $^{51}$Cr-labeled target cells without an in vitro stimulation were performed. As shown in FIG. 2D, after vaccination with STxB-OVA (1 μg) mixed with α-GalCer, large numbers of CD8$^+$T cells produced IFNγ (mean $61/10^5$ cells) when co-incubated with OVA$_{257-264}$ peptide-pulsed EL4 cells (FIG. 2D left). Similarly, as shown in FIG. 1D (right), spleen cells from mice immunized with STxB-OVA mixed with α-GalCer efficiently lyzed EL4 target cells loaded with the OVA$_{257-264}$ peptide, whereas no cytotoxicity was observed against EL4 alone. No ex vivo cytotoxicity was demonstrated when mice were vaccinated twice with STxB-OVA alone even when high doses (50 μg) were used (data not shown).

To check whether these results could be reproduced with another more clinically relevant antigen, mice were immunized twice with STxB coupled to a polypeptide derived from the HPV16-E7 protein (STxB-E7$_{43-57}$) at a low dose (1 μg). A marked induction of anti-E7 CTL detectable ex vivo by the E7$_{49-57}$ Db tetramer (1.12% of CD8$^+$T cells) was also demonstrated (FIG. 3). These CTL were functional (data not shown). In contrast, at this dosage, only low levels of E7-specific CTL (0.12% of CD8$^+$T cells) were detected after immunization with STxB-E7$_{43-57}$ alone. The E7$_{43-57}$ polypeptide mixed with α-GalCer did not prime a CTL response (FIG. 3).

We then investigated whether the synergy observed between α-GalCer and STxB was restricted to induction of CTL or could be extended to other immune responses. Mice vaccinated with the STxB-OVA conjugate mixed with α-GalCer displayed a more potent anti-OVA CD4$^+$T cell response compared to mice immunized with STxB-OVA alone or free ovalbumin mixed with IFA (FIG. 4). However, although α-GalCer increased the anti-OVA IgG2a response compared to free ovalbumin with adjuvant, this humoral response either for total IgG or the various isotypes was not enhanced when STxB was admixed with α-GalCer compared to STxB alone. Analysis of Potential Mechanisms Leading to the Synergy Between StxB and α-GalCer.

In a previous study, the adjuvant property of α-GalCer was related to its ability to promote maturation of DC. A rapid increase of costimulatory molecules (CD86 . . . ) and MHC class II was observed, after administration of α-GalCer in mice (data not shown). However, we also confirmed that other adjuvants used in this study (CpG, Poly (I:C) . . . ) also activated dendritic cells but their enhancing effect on the STxB immunogenicity remained modest (FIG. 1 and data not shown).

Since the levels of CD1d may affect NKT cell activation, we tested whether STxB could modulate the expression of CD1d. After STxB administration in mice, no significant change was detected in CD1d expression on APC (dendritic cells and B cells) derived from splenocytes. Similarly, α-GalCer did not regulate the membrane expression of $Gb_3$ on dendritic and B cells (data not shown).

As one striking consequence of the synergy between STxB and α-GalCer is the ability to markedly reduce the efficient dose of STxB vaccine, we analyzed the in vivo presentation of antigen after vaccination. Dendritic cells derived from mice immunized with low doses of STxB-OVA (1 μg) combined with α-GalCer, 7 days ealier, more significantly presented the $OVA_{257-264}/K^b$ complex in vivo than mice vaccinated with STxB alone (FIG. 5). This presentation was observed for both dendritic cells derived from spleen or draining lymph node and persisted for at least 12 days (data not shown). This increased presentation could also be detected when STxB was mixed with other adjuvants, but the levels of antigen presentation appeared to be lower than those observed with α-GalCer (FIG. 5 and data not shown). Although the $Gb_3$ receptor and CD1d are also expressed by B cells, addition of α-GalCer to STxB-OVA did not allow these cells to express the $OVA_{257-264}/K^b$ complex whose expression remained restricted to dendritic cells after immunization as previously reported (data not shown).

STxB Conjugate Mixed with α-GalCer Broke Tolerance Against Self Antigens

It is often criticized that exogenous antigens such as ovalbumin and viral proteins do not mimic the clinical situations in which therapeutic vaccines will be developed because most tumor antigens are self antigens and, during chronic infection, tolerance to viral protein is already established. For these indications, a potential vaccine is therefore expected to be endowed with the ability to break tolerance against self antigen. For this purpose we selected a novel transgenic mouse model that expresses ovalbumin on the surface of all cells. When these mice were vaccinated with STxB-OVA alone, no anti-$OVA_{257-264}$ $CD8^+$T cell induction was observed in either blood or spleen at various times after primary or secondary immunizations (FIG. 6 and data not shown). In contrast, specific tetramer assay detected significant levels of anti-$OVA_{257-264}$ $CD8^+$T cells in 8 out of 11 mice immunized with STxB-OVA combined with α-GalCer (FIG. 6). Some of them (4 out of 7 vaccinated mice) were functional as they produced IFNγ using an Elispot assay. These specific $CD8^+$T cells seemed to be induced by the vaccine as they were not present before immunization (data not shown). These anti-OVA specific $CD8^+$ T cells were essentially found after primary immunizations and rapidly disappeared from the blood and from the spleen. It should be emphasized that this strain of mice expresses membrane ovalbumin in all organs.

STxB Conjugate Mixed with α-GalCer Induces Anti-Viral Protective Immunity.

To investigate the clinical relevance of the synergy observed between STxB and α-GalCer, we challenged mice with recombinant vaccinia virus encoding ovalbumin (VV-OVA), 7 days after vaccination, and measured virus titers in the ovaries 5 days later to assess protection. Vaccination of mice with STxB-OVA and α-GalCer conferred potent protection against VV-OVA, with virus titers in the ovaries reduced by 5 log($3.92.10^3$ PFU) compared to those of mice treated with PBS ($8.28.10^8$ PFU) (FIG. 7). Immunization with STxB-OVA alone conferred a statistically significant reduction of virus titers in the ovary by >2 log but this effect was dramatically amplified by the addition of α-GalCer. To exclude a direct role of α-GalCer in this anti-viral protection, we showed that mice immunized with ovalbumin and α-GalCer exhibited a slight reduction of infectious virus titers from $8.28.10^8$ PFU in PBS-treated mice to $7.73.10^8$ PFU corresponding to less that 1 log reduction of virus titers (FIG. 7). The specificity of the protection was documented by challenging STxB-OVA/α-GalCer immunized mice, with an irrelevant vaccinia virus encoding hepatitis B×protein). No significant reduction of viral load was observed (data not shown).

No Adjuvant Effect of α-GalCer in Mice Deficient in NKT Cells.

Ja $18^{-/-}$ mice were immunized with STxB-OVA (1 μg) or STxB-OVA+α-GalCer (2 μg) 7 days after immunization, the spleens of immunized and non-immunized mice were harvested and stained with anti-CD8 antibody and $OVA_{257-264}/K^b$ tetramer. The results (FIG. 8) showed that almost no anti-$OVA_{257-264}$ specific CTL were observed in immunized Ja$18^{-/-}$ mice with or without α-GalCer. This is to be compared with the 6.43% of anti-$OVA_{257-264}$ specific CTL observed in immunized C57BL/6 mice with α-GalCer (FIG. 2A). Therefore, no adjuvant effect of α-GalCer can be observed in mice deficient in NKT cells, confirming the role of the activation of NKT cells in the adjuvant mechanism of α-GalCer.

Vaccination with αGalCer Combined with STxB-Ova Induces Protection Against Established Tumors C57BL6 mice were grafted with EG7 tumor, a thymoma transfected with cDNA encoding ovalbumin mice, and three days after were treated with PBS, 5 μg STx-B-Ova, 2 μg αGalCer or the combination of both (FIG. 9).

Mice vaccinated three days after subcutaneous graft of EG7 with the combination of STxB-Ova and αGalCer, showed a significant regression of tumor. In contrast mice immunized with STxB-Ova alone or αGalCer alone did not control the growth of the tumor.

Vaccination with C-αGalCer Combined with StxB-Ova Induces Protection Against Established Tumors C57BL6 mice are grafted with EG7 tumor, a thymoma transfected with cDNA encoding ovalbumin mice, and three days after are treated with PBS, 5 μg STx-B-Ova, 2 μg C-αGalCer, or the combination STx-B-Ova/C-αGalCer.

Mice vaccinated three days after subcutaneous graft of EG7 with the combination of STx-B-Ova/C-αGalCer will show a significant regression of tumor. In contrast mice immunized with STxB-Ova, or C-αGalCer alone will not control the growth of the tumor.

The invention claimed is:

1. A composition comprising
    a) a B subunit of Shiga toxin or a functional equivalent thereof which binds to the Gb3 receptor, complexed with an antigen and
    b) at least one ligand of CD1 that stimulates NK T cells wherein said ligand is a glycolipid, a phospholipid, a glycosphingolipid, a derivative or an analog thereof, wherein said composition breaks tolerance against self antigens and stimulates dendritic cells and wherein there is synergy between said B subunit of Shiga toxin or a functional equivalent thereof which binds to the Gb3 receptor, complexed with an antigen and said at least one ligand of CD1 that stimulates NK T cells.

2. The composition according to claim 1, wherein the functional equivalent of the B subunit of Shiga toxin which binds to the Gb3 receptor has at least 60% amino acid sequence identity to the B subunit of Shiga toxin.

3. The composition according to claim 1, wherein said ligand of CD1 is a ligand of CD1d.

4. The composition according to claim 1, wherein said ligand is chosen from disialoganglioside (GD3), phosphotidylethanolamine (PEI) or phosphatidylinositol (PI).

5. The composition according to claim 1, wherein said ligand is a glycosylceramide or an analog or a derivative thereof.

6. The composition according to claim 5, wherein said glycosylceramide is selected from the group consisting of α-GalCer, α-GlcCer, Galα1-6Galα1-1'Cer, Galα1-6Glcα1-1'Cer, Galα1-2Galα1-1'Cer, Galα1-3Galα1-1'Cer and a derivative thereof.

7. The composition according to claim 5, wherein the glycosylceramide α-GalCer is (2S,3S,4S)-1-O-(α-D-galactopyranosyl)-2-(N-hexacosanoylamino)-1,3,4,-octadecanetriol.

8. The composition according to claim 5, wherein the glycosylceramide α-GalCer is (2S,3S,4S)-1-O-(α-D-galactopyranoxy)-2-(N-hexacosanoylamino)-3,4,-octadecanetriol (KRN7000).

9. The composition according to claim 5, wherein said ligand is selected from the group consisting of 3-O-sulfo-α-GalCer, α-GalCer, and OCR compound and α-C-GalCer.

10. The composition according to claim 5, wherein said glycosylceramide is α-C-GalCer.

11. The composition according to claim 5, wherein said glycosylceramide is PBA-57.

12. The composition according to claim 1, wherein said ligand is a microbe derived glycolipid.

13. The composition according to claim 1, wherein said ligand is
    a *Sphingomonas* species-derived glycosphingolipid selected from the group consisting of GSL-1 and GaL'1 or
    a *Borrelia* species derived glycolipid selected from the group consisting of BbGL-I and BgGL-II or
    a *Mycobacteria* species derived phosphoglycolipid PIM.

14. The composition according to claim 1, wherein the B subunit of Shiga toxin or the functional equivalent thereof is present in a universal polypeptidic carrier having the formula STxB-Z(n)-Cys, wherein
    StxB is the Shiga Toxin B subunit or a functional equivalent thereof which binds to the Gb3 receptor,
    Z is an amino acid devoid of a sulfhydryl group, n being 0.1 or a polypeptide,
    Cys is the amino acid Cysteine.

15. The composition according to claim 14, wherein n is 0.

16. The composition according to claim 14, wherein the antigen is covalently linked to the —S residue of the universal carrier by a —S—S, or —S—CO or —S—CH$_2$, or —S—NH linkage.

17. The composition according to claim 14, wherein the universal carrier is covalently linked to an oligopeptide or a polypeptide by a —S—S, or —S—CO or —S—CH$_2$, or —S—NH linkage, and the antigen to be targeted is operably linked to said oligopeptide or polypeptide.

18. The composition according to claim 14, wherein the universal carrier is covalently linked to a poly-lysine oligopeptide moiety and the antigen to be targeted is operably linked to said poly-lysine moiety.

19. The composition according to claim 1, wherein the antigen is a tumor antigen, a viral antigen or a bacterial antigen.

20. The composition according to claim 1, further comprising a pharmaceutically acceptable carrier.

21. A medicament comprising a composition according to claim 1.

22. A pharmaceutical kit comprising:
a first container comprising a B subunit of Shiga toxin or a functional equivalent thereof which binds to the Gb3 receptor, complexed with an antigen and
a) at least a second container comprising at least one ligand of CD1 that stimulates NK T cells wherein said ligand is a glycolipid, a phospholipid, a glycosphingolipid, a derivative or an analog thereof.

23. The composition according to claim 6, wherein said derivative is a C glycoside derivative or a C glycoside derivative of a α-GalCer.

24. A composition comprising
a) a B subunit of Shiga toxin or a functional equivalent which binds to the Gb3 receptor thereof which is able to bind the Gb3 receptor, complexed with an antigen and
b) α-GalCer that stimulates NK T cells, wherein said composition breaks tolerance against self antigens, stimulates dendritic cells and elicits antiviral immunity, wherein there is synergy between said B subunit of Shiga toxin or a functional equivalent thereof which binds to the Gb3 receptor, complexed with an antigen and said α-GalCer that stimulates NK T cells.

* * * * *

UNITED STATES PATENT AND TRADEMARK OFFICE
CERTIFICATE OF CORRECTION

PATENT NO.         : 8,685,408 B2
APPLICATION NO.    : 12/521404
DATED              : April 1, 2014
INVENTOR(S)        : Eric Tartour Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 876 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 90
<212> TYPE: PRT
<213> ORGANISM: Artificial Sequence
<220> FEATURE:
<223> OTHER INFORMATION: B subunit of Shiga toxin

<400> SEQUENCE: 1

Met Lys Lys Thr Leu Leu Ile Ala Ala Ser Leu Ser Phe Phe Ser Ala
1               5                   10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg Cys
                85                  90
```